United States Patent [19]
Hannett

[11] Patent Number: 5,908,696
[45] Date of Patent: *Jun. 1, 1999

[54] AROMATIC STICKS

[76] Inventor: Dominic Hannett, Threlkeld House, 159 The Green, Eccleston, Chorley Lancashire, United Kingdom, PR7 5SA

[ * ] Notice: This patent issued on a continued prosecution application filed under 37 CFR 1.53(d), and is subject to the twenty year patent term provisions of 35 U.S.C. 154(a)(2).

[21] Appl. No.: 08/840,183

[22] Filed: Apr. 11, 1997

[30] Foreign Application Priority Data

Apr. 11, 1996 [GB] United Kingdom .................... 9607535

[51] Int. Cl.$^6$ ........................................................ A61K 7/46
[52] U.S. Cl. ........................ 428/375; 428/537.1; 428/535; 422/126

[58] Field of Search .................................. 428/535, 537.1, 428/375; 422/126

[56] References Cited

FOREIGN PATENT DOCUMENTS 1049790  3/1991  China .............................. A61L 9/02
54-8734  1/1979  Japan .

OTHER PUBLICATIONS

Abstract of JP 54008734, Jan. 1979.

*Primary Examiner*—Alexander Thomas
*Attorney, Agent, or Firm*—Jenkins & Wilson, P.A.

[57] ABSTRACT

An aromatic stick comprises a pine spill to which is adhered a covering of peat dust, in order to produce the smell of burning peat when smouldering.

5 Claims, No Drawings

AROMATIC STICKS

The present invention relates to aromatic sticks designed to give off an aroma when burned, as joss-sticks do.

Conventionally, joss-sticks are made by gluing wood dust to a bamboo spill and dipping the resultant stick in an aromatic oil so that the dust is impregnated with the essence, such as jasmine or sandalwood. When lit, the stick smoulders and produces a scented fume.

The present invention has been made in order to provide an aromatic stick which is a "Celtic" alternative to the conventional "oriental" joss-stick.

According to a first aspect of the present invention there is provided an aromatic stick comprising a wood spill and peat, the peat being secured to the spill by means of adhesive.

Thus, the invention provides an aromatic stick which is environmentally friendly and which, when smouldering, produces the natura smell a of burning peat. The stick of the invention does not require impregnation with an essence. Thus, the aroma produced by the stick of the invention is natural and does not have the perfume effect of conventional joss-sticks. The stick of the invention will appeal to those desiring a natural, traditional cottage aroma. Furthermore, the stick can be easily produced in northern countries where the materials required are readily available.

Preferably the wood spill comprises softwood and most preferably the wood spill is a pine spill. In particular, pine is indigenous and thus readily available in northern countries, whereas bamboo is necessarily imported into such countries. Softwood is preferred since it is fast-growing and pine, in particular, is preferred to other indigenous woods since it has a straight grain so that pine spills can be produced more easily.

Preferably the peat is particulate or comprises peat dust. Preferably the adhesive is cellulose- or starch-based such as conventional wall paper paste. Thus, the adhesive is preferably naturally biodegradable and non-toxic as opposed to, for example, a resin-based glue which is potentially toxic.

The stick of the invention may be produced by applying adhesive to the wood spill and then applying peat dust to the adhesive and allowing the adhesive to dry. The process may then be repeated in order to build up a sufficient bulk of peat dust. The adhesive may be sprayed onto the spill and the dust may be blown onto the adhesive. Thicker dust particles may be applied first, followed by finer dust particles which light more easily. Further adhesive may be sprayed on between successive layers of peat dust.

The aromatic stick of the invention will typically be designed to light and smoulder as easily as, and in use will not produce any more residue than, conventional joss-sticks.

According to a second aspect of the invention there is provided a method of producing an aromatic stick by securing peat to a wood spill by means of adhesive.

In a specific embodiment of the invention, the aromatic stick comprises a pine spill having one or more layers of starch-based adhesive securing one or more layers of peat dust to the spill or to successive layers of the dust.

It will be appreciated that the present invention is not intended to be restricted to the details of the above embodiment which is described by way of example only.

I claim:

1. An aromatic stick comprising a wood spill and peat, the peat being secured to the spill by means of adhesive, and the stick being free of impregnation with an aromatic essence.

2. An aromatic stick according to claim 1, wherein the spill is a pine spill.

3. An aromatic stick according to claim 1, wherein the peat comprises peat dust secured to the spill.

4. An aromatic stick according to claim 3, comprising a plurality of layers of peat dust and a plurality of layers of adhesive.

5. A method of producing an aromatic stick in accordance with claim 1, comprising securing peat to a wood spill by means of adhesive.

* * * * *